US012687551B2

(12) United States Patent
Kobold et al.

(10) Patent No.: US 12,687,551 B2
(45) Date of Patent: Jul. 21, 2026

(54) METHOD FOR DETERMINING GLYCATED HEMOGLOBIN A (HBA1C) BY MASS SPECTROMETRY

(71) Applicant: Roche Diagnostics Operations, Inc., Indianapolis, IN (US)

(72) Inventors: Uwe Kobold, Weilheim (DE); Andreas Leinenbach, Oberhausen (DE); Indranil Mitra, Munich Süd (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1037 days.

(21) Appl. No.: 17/370,170

(22) Filed: Jul. 8, 2021

(65) Prior Publication Data

US 2021/0333290 A1    Oct. 28, 2021

Related U.S. Application Data

(63) Continuation of application No. PCT/EP2020/051039, filed on Jan. 16, 2020.

(30) Foreign Application Priority Data

Jan. 17, 2019    (EP) .................................... 19152309

(51) Int. Cl.
*G01N 33/72*      (2006.01)
*G01N 33/68*      (2006.01)
*G01N 33/78*      (2006.01)

(52) U.S. Cl.
CPC ....... *G01N 33/723* (2013.01); *G01N 33/6848* (2013.01)

(58) Field of Classification Search
CPC .......................... G01N 33/723; G01N 33/6848
See application file for complete search history.

(56) References Cited

U.S. PATENT DOCUMENTS

| | | | |
|---|---|---|---|
| 7,641,862 B2 | 1/2010 | Noetzel et al. | |
| 2008/0108144 A1* | 5/2008 | Alam ....................... | G01N 1/34 435/7.1 |
| 2009/0246814 A1* | 10/2009 | Kobold ................ | G01N 33/723 435/71.1 |
| 2015/0126402 A1* | 5/2015 | Shabb ................ | G01N 33/6848 436/86 |
| 2017/0176463 A1* | 6/2017 | Manneh ................ | G01N 33/723 |
| 2018/0128721 A1* | 5/2018 | Tikanoja ................ | G01N 1/405 |

FOREIGN PATENT DOCUMENTS

| | | |
|---|---|---|
| EP | 0881494 A1 | 12/1998 |
| EP | 1445020 A1 | 8/2004 |
| WO | 2008009445 A1 | 1/2008 |
| WO | 2009067421 A1 | 5/2009 |
| WO | 2015112429 A1 | 7/2015 |
| WO | 2017103180 | 6/2017 |

OTHER PUBLICATIONS

Pundir. Determination of glycated hemoglobin with special emphasis on biosensing methods. 2014. (Year: 2014).*
Jeong. Optimization of Enzyme Digestion Conditions for Quantification of Glycated Hemoglobin Using Isotope Dilution Liquid Chromatography-Tandem Mass Spectrometry. 2014 (Year: 2014).*
Agilent Technologies; Keys for Enabling Optimum Peptide Characterizations: A Peptide Mapping "How to" Guide. Printed in the USA, Apr. 25, 2014. 24-pages.
Benjamin et al., Glycated Protein Update: Implications of Recent Studies, Including the Diabetes Control and Complications Trial; Clin. Chem., 1994, vol. 40, No. 5, pp. 683-687.
Goldstein et al., Is Glycohemoglobin Testing Useful in Diabetes Mellitus: Lessons form the Diabetes Control and Complications Trial; Clin. Chem., 1994, vol. 40, No. 8, pp. 1637-1640.
Jeong, Ji-Seon, Optimization of Enzyme Digestion Conditions for Quantification of Glycated Hemoglobin Using Isotope Dilution Liquid Chromatography-Tandem Mass Spectrometry; Mass Spectrometry Letters, 2014, vol. 5, No. 2, 5-pages.
Jeppsson et al., Approved IFCC Reference Method for the Measurement of HbA1c in Human Blood; Clin Chem Lab Med, 2002, vol. 40, No. 1, pp. 78-89.
Kaiser et al., Modified HPLC-Electrospray Ionization/Mass Spectrometry Method for HbA1cBased on IFCC Reference Measurement Procedure; Clinical Chemistry, 2008, vol. 54, No. 6, pp. 1018-1022.
Li et al., Shielding of protein-boronate interactions during boronate chromatography of neoglycoproteins; Journal of Chromatography A; 2001, vol. 909, pp. 137-145.
Nathan et al., The Effect of Intensive Treatment of Diabetes n the Development and Progression of Long-Term Complications in Insulin-Dependent Diabetes Mellitus; The New England Journal of Medicine; 1993, vol. 329, No. 14, 10-pages.
Santiago et al., Perspectives in Diabetes; Lessons from the Diabetes Control and Complications Trial; Diabetes, 1993, vol. 42, 6-pages.
Zhang et al., Bridge life cycle assessment with data uncertainty; Int. J. Life Cycle Assess, 2016, vol. 21, pp. 569-576.
Biroccio et al., A quantitative method for the analysis of glycated and glutathionylated hemoglobin by matrix-assisted laser desorption inonization-time of flight mass spectrometry; Analytical Biochemistry; 2005, vol. 336, pp. 279-288.
Li et al., Association of serum lipid metabolism with markers of urinary peptides in type 2 diabetes patients; Int. J. Clin. Exp. Pathol., 2016, vol. 9, No. 1, pp. 37-48.
Li et al., Application of shielding boronate affinity chromatography in the study of the glycation pattern of haemoglobin; Journal of Chromatography B; 2002, vol. 776, pp. 149-160.

(Continued)

*Primary Examiner* — Rebecca M Fritchman
(74) *Attorney, Agent, or Firm* — Taft Stettinius & Hollister LLP

(57)        ABSTRACT

The present invention refers to a method for determining peptide fragments of glycated hemoglobin A (HbA1c) molecules by mass spectrometry (MS), a reagent kit, and a clinical diagnostic system adapted for performing the method.

10 Claims, 3 Drawing Sheets

Specification includes a Sequence Listing.

(56) References Cited

OTHER PUBLICATIONS

Vesper et al., Assessment of microwave-assisted enzymatic digestion by measureing glycated hemoglobin A1c by mass spectrometry; Rapid Communications in Mass Spectometry; 2005, vol. 19, pp. 2865-2870.

Willekens et al., Quantification of Glycohemoglobin in Blood by Mass Spectometry Applying Multiple-Reaction Monitoring; Clinical Chemistry, vol. 46, No. 2, 3-pages.

Zhang et al., Quantification of hemoglobin A1c by off-line HPLC separation and liquid chromatography-tandem mass spectrometry: a modification of the IFCC reference measurement procedure; Clin Chem Lab Med, 2016, vol. 54, No. 4, pp. 569-576.

International Search Report, European Patent Office, International Patent Application No. PCT/EP2020/051039, Mar. 16, 2020, 5 pages.

Written Opinion of the International Searching Authority, European Patent Office, International Patent Application No. PCT/EP2020/051039, Mar. 16, 2020, 6 pages.

International Preliminary Report on Patentability, European Patent Office, International Patent Application No. PCT/ EP2020/051039, Jun. 16, 2021, 7 pages.

Li et al., Application of shielding boronate affinity chromatography in the study of the glycation pattern of haemoglobin, J. Chromatogr. B., vol. 776, 2002, pp. 149-160.

* cited by examiner

SEQUENCE LISTING

<160> NUMBER OF SEQ ID NOS: 1

<210> SEQ ID NO 1
<211> LENGTH: 16
<212> TYPE: PRT
<213> ORGANISM: Homo sapiens
<400> SEQUENCE: 1

Val His Leu Thr Pro Glu Glu Lys Ser Ala Val Thr Ala Leu Trp Gly
1           5                10               15

METHOD FOR DETERMINING GLYCATED HEMOGLOBIN A (HBA1C) BY MASS SPECTROMETRY

This application is a U.S. Continuation Application of International Application No. PCT/EP2020/051039 filed Jan. 16, 2020, claiming priority to European Application No. 19152309.1 filed Jan. 17, 2019, the disclosures of which are hereby incorporated by reference in their entirety.

DESCRIPTION

The present invention refers to a method for determining peptide fragments of glycated hemoglobin A (HbA1c) molecules by mass spectrometry (MS), a reagent kit, and a clinical diagnostic system adapted for performing the method.

BACKGROUND OF THE INVENTION

Impaired control of circulating blood glucose levels is an indicator of diabetes. Blood glucose may attach in a non-enzymatic statistical process to the lysine residues of poly-peptides thereby leading to glycated polypeptides. In the case of hemoglobin A (HbA), a reaction occurs between glucose and the N-terminus of the β-chain. The resulting glycated hemoglobin A β-chain has been designated as HbA1c.

HbA1c is the major glycated hemoglobin species in human blood. The comprehensive Diabetes Control and Complications Trial (DCCT) has provided evidence that complications such as retinopathy, nephropathy and neuropathy are directly related to the degree of hyperglycemia in patients with insulin-dependent diabetes (IDDM), and has shown that the measurement of HbA1c in blood is an excellent tool for long-term monitoring of the glycemic state of diabetes patients (Nathan et al., N. Engl. J. Med 329 (1993) 977-986; Santiago, J. V., Diabetes 42 (1993) 1549-1554; Benjamin, J. and Sacks, D. B., Clin. Chem. 40 (1994) 683-687; and Goldstein D. et al., Clin. Chem 40 (1994) 1637-1640). The DCCT study has also clearly demonstrated the need for reliable and reproducible measurement of HbA1c and HbA0—the non-glycated hemoglobin, respectively.

There are numerous different methods for determining glycated hemoglobin, namely physico-chemical methods including chromatography and/or mass spectrometry (MS), chemical methods and immunological methods. A reference method for the measurement of HbA1c in human blood which has been approved by the International Federation of Clinical Chemistry and Laboratory Medicine (IFCC) comprises enzymatic cleavage of hemoglobin into peptides by the enzyme endoproteinase Glu-C for a time period of 18-20 h and subsequently separating and quantifying glycated and non-glycated N-terminal hexapeptides of the β-chain by HPLC and electrospray ionization mass spectrometry or in a two-dimensional approach using HPLC and capillary electrophoresis with UV-detection (Jeppsson et al., Clin. Chem. Lab. Med. 40 (2002), 78-89).

Modifications of this reference method have been described by Kaiser et al. (Clin. Chem. 54 (2008), 1018-1022; Li et al., J. Chromatogr. B. 776 (2002), 149-160; Jeong (Mass Spectrom. Lett. 5 (2014), 52-56; and Zhang et al., Clin. Chem. Lab Med. 54 (2016), 569-576), all referring to a proteolytic digestion for a time period of at least 18 h.

Thus, known methods involving enzymatic digestion of hemoglobin A usually require an overnight incubation in order to obtain a sufficient amount of cleavage products and thus stable measurement signals. Further, a separation of complex peptide mixtures including matrix components with conventional chromatography is required before subjecting the sample to the MS detection. These methods are thus time-consuming and of limited use for high-throughput measurements of patient samples.

Thus, there is a need for providing a rapid and reliable method for determining HbA1c by MS.

SUMMARY OF THE INVENTION

A first aspect of the present invention refers to a method for determining glycated hemoglobin A (HbA1c) in a sample, comprising:
- (a) providing a sample comprising hemoglobin A (HbA) molecules,
- (b) subjecting the sample from step (a) to a partial proteolytic digestion step wherein N-terminal fragments of hemoglobin A β-chain molecules are generated,
- (c) optionally enriching the N-terminal fragments of hemoglobin A β-chain molecules generated in step (b), and
- (d) subjecting the sample comprising N-terminal fragments of hemoglobin A β-chain molecules to an analysis by mass-spectrometry (MS) wherein the amount or concentration of HbA1c in the sample is determined.

A second aspect of the present invention refers to a kit, comprising
- (i) an enzyme for the partial proteolytic digestion of HbA β-chain molecules and optionally a digestion buffer for said enzyme,
- (ii) a stopping medium, which is capable of stopping a proteolytic digestion with the enzyme of (i), and
- (iii) optionally enrichment means for enriching the proteolytically digested HbA1c molecules, and
- (iv) optionally an elution medium comprising an organic water-miscible solvent for use in eluting sample components from the enrichment means of (iii).

The kit is particularly suitable for use in a method as described above.

In a third aspect of the invention a diagnostic system is provided which is adapted for performing the method as described above. The diagnostic system is particularly for use together with the kit as described above.

The present invention allows rapid and reliable determination of proteolytically digested glycated HbA1c molecules and optionally proteolytically digested non-glycated HbA0 molecules in a sample by MS.

DETAILED DESCRIPTION

Definitions

Figure 1A:
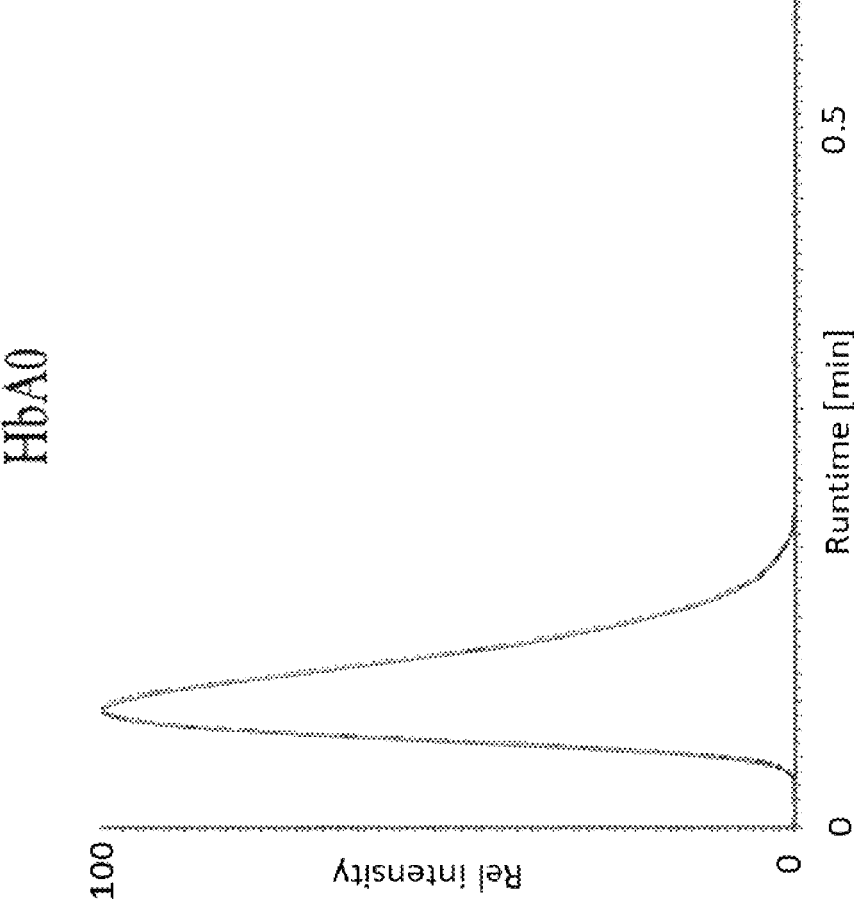
FIGS. 1A & 1B depict the MS/MS peaks from HbA1c (FIG. 1A) and HbA0 (FIG. 1B) peptides obtained by digestion of a whole blood sample with Glu-C.

The word "comprise", and variations such as "comprises" and "comprising", will be understood to imply the inclusion of a stated integer or step or group of integers or steps but not the exclusion of any other integer or step or group of integers or steps.

As used in this specification and the appended claims, the singular forms "a", "an", and "the" include the respective terms also in plural, unless the content clearly dictates otherwise.

Percentages, concentrations, amounts, and other numerical data may be expressed or presented herein in a "range" format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "4% to 20%" should be interpreted to include not only the explicitly recited values of 4% to 20%, but to also include individual values and sub-ranges within the indicated range. Thus, included in this numerical range are individual values such as 4, 5, 6, 7, 8, 9, 10, . . . 18, 19, 20% and sub-ranges such as from 4-10%, 5-15%, 10-20%, etc. This same principle applies to ranges reciting minimal or maximal values. Furthermore, such an interpretation should apply regardless of the breadth of the range or the characteristics being described.

The term "about" when used in connection with a numerical value is meant to encompass numerical values within a range having a lower limit that is 5% smaller than the indicated numerical value and having an upper limit that is 5% larger than the indicated numerical value.

The term "Mass Spectrometry" ("Mass Spec" or "MS") relates to an analytical technology used to identify compounds by their mass. MS is a method of filtering, detecting, and measuring ions based on their mass-to-charge ratio, or "m/z". MS technology generally includes (1) ionizing compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). The term "ionization" or "ionizing" refers to the process of generating an analyte ion having a net electrical charge equal to one or more electron units. Negative ions are those having a net negative charge of one or more electron units, while positive ions are those having a net positive charge of one or more electron units. The MS method may be performed either in "negative ion mode", wherein negative ions are generated and detected, or in "positive ion mode" wherein positive ions are generated and detected.

"Tandem mass spectrometry" or "MS/MS" involves multiple steps of mass spectrometry selection and detection, wherein fragmentation of the analyte occurs in between the steps. In a tandem mass spectrometer, ions are formed in the ion source and separated by mass-to-charge ratio in the first stage of mass spectrometry (MS1). Ions of a particular mass-to-charge ratio (precursor ions or parent ions) are selected and fragment ions (or daughter ions) are created by collision-induced dissociation, ion-molecule reaction, and/ or photodissociation. The resulting ions are then separated and detected in a second stage of mass spectrometry (MS2).

Most sample workflows in MS further include sample preparation and/or enrichment steps, wherein e.g. the analyte(s) of interest are separated from the matrix, e.g. sample constituents different from the analyte, using e.g. gas or liquid chromatography. Typically, for the mass spectrometry measurement, the following three steps are performed:

(1.) a sample comprising an analyte of interest is ionized, usually by adduct formation with cations, often by protonation to cations. Ionization sources include but are not limited to electrospray ionization (ESI) and atmospheric pressure chemical ionization (APCI).

(2.) the ions are sorted and separated according to their mass and charge. High-field asymmetric-waveform ion-mobility spectrometry (FAIMS) may be used as ion filter.

(3.) the separated ions are then detected, e.g. in multiple reaction mode (MRM), and the results are displayed on a chart.

The term "electrospray ionization" or "ESI," refers to methods in which a solution is passed along a short length of capillary tube, to the end of which is applied a high positive or negative electric potential. A solution reaching the end of the tube is vaporized (nebulized) into a jet or spray of very small droplets of solution in solvent vapour. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

The term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. The ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar entity.

"Multiple reaction mode" or "MRM" is a detection mode for a MS instrument in which a precursor ion and one or more fragment ions are selectively detected.

Since a mass spectrometer separates and detects ions of slightly different masses, it easily distinguishes different isotopes of a given element. Mass spectrometry is thus, an important method for the accurate mass determination and characterization of analytes, including but not limited to low-molecular weight analytes, peptides, polypeptides or proteins. Its applications include the identification of proteins and their post-translational modifications, the elucidation of protein complexes, their subunits and functional interactions, as well as the global measurement of proteins in proteomics. De novo sequencing of peptides or proteins by mass spectrometry can typically be performed without prior knowledge of the amino acid sequence.

Mass spectrometric determination may be combined with additional analytical methods including chromatographic methods such as gas chromatography (GC), liquid chromatography (LC), particularly HPLC, and/or ion mobility-based separation techniques.

In the context of the present disclosure, the terms "analyte", "analyte molecule", or "analyte(s) of interest" are used interchangeably referring to the chemical species to be analysed via mass spectrometry. Chemical species suitable to be analysed via mass spectrometry, i.e. analytes, can be any kind of molecule present in a living organism, include but are not limited to nucleic acids (e.g. DNA, mRNA, miRNA, rRNA etc.), amino acids, peptides, proteins (e.g. cell surface receptor, cytosolic protein etc.), metabolites or hormones (e.g. testosterone, estrogen, estradiol, etc.), fatty acids, lipids, carbohydrates, steroids, ketosteroids, secosteroids (e.g. Vitamin D), molecules characteristic of a certain modification of another molecule (e.g. sugar moieties or phosphoryl residues on proteins, methyl-residues on genomic DNA) or a substance that has been internalized by the organism (e.g. therapeutic drugs, drugs of abuse, toxin, etc.) or a metabolite of such a substance. Such analyte may serve as a biomarker. In the context of present invention, the term "biomarker" refers to a substance within a biological system that is used as an indicator of a biological state of said system.

Analytes may be present in a sample of interest, e.g. a biological or clinical sample. The terms "sample" or "sample of interest" are used interchangeably herein, referring to a part or piece of a tissue, organ or individual, typically being smaller than such tissue, organ or individual, intended to represent the whole of the tissue, organ or individual. Upon analysis a sample provides information about the tissue status or the health or diseased status of an organ or individual. Examples of samples include but are not limited to fluid samples such as blood, serum, plasma, synovial fluid, spinal fluid, urine, saliva, and lymphatic fluid, or solid samples such as dried blood spots and tissue extracts. Further examples of samples are cell cultures or tissue cultures.

In the context of the present disclosure, the sample may be derived from an "individual" or "subject". Typically, the subject is a mammal. Mammals include, but are not limited to, domesticated animals (e.g., cows, sheep, cats, dogs, and horses), primates (e.g., humans and non-human primates such as monkeys), rabbits, and rodents (e.g., mice and rats).

Before being analysed via Mass Spectrometry, a sample may be pre-treated in a sample- and/or analyte specific manner. In the context of the present disclosure, the term "pre-treatment" refers to any measures required to allow for the subsequent analysis of a desired analyte via Mass Spectrometry. Pre-treatment measures typically include but are not limited to the elution of solid samples (e.g. elution of dried blood spots), the addition of a hemolyzing reagent (HR) to whole blood samples, and the addition of an enzymatic reagent to urine samples. Also the addition of internal standards (ISTD) is considered as pre-treatment of the sample.

The term "hemolysis reagent" (HR) refers to reagents which lyse cells present in a sample. In the context of this invention hemolysis reagents in particular refer to reagents which lyse the cells present in a blood sample including but not limited to the erythrocytes present in whole blood samples. A well-known hemolysis reagent is water ($H_2O$), e.g. deionized or distilled water. Further examples of hemolysis reagents include but are not limited to liquids with high osmolarity (e.g. 8M urea), ionic liquids, and different detergents.

Typically, an internal standard (ISTD) is a known amount of a substance which exhibits similar properties as the analyte of interest when subjected to the mass spectrometric detection workflow (i.e. including any pre-treatment, enrichment and actual detection step). Although the ISTD exhibits similar properties as the analyte of interest, it is still clearly distinguishable from the analyte of interest. Exemplified, during chromatographic separation, such as gas or liquid chromatography, the ISTD has about the same retention time as the analyte of interest from the sample. Thus, both the analyte and the ISTD enter the mass spectrometer at the same time. The ISTD however, exhibits a different molecular mass than the analyte of interest from the sample. This allows a mass spectrometric distinction between ions from the ISTD and ions from the analyte by means of their different mass/charge (m/z) ratios. Both are subject to fragmentation and provide daughter ions. These daughter ions can be distinguished by means of their m/z ratios from each other and from the respective parent ions. Consequently, a separate determination and quantification of the signals from the ISTD and the analyte can be performed. Since the ISTD has been added in known amounts, the signal intensity of the analyte from the sample can be attributed to a specific quantitative amount of the analyte. Thus, the addition of an ISTD allows for a relative comparison of the amount of analyte detected, and enables unambiguous identification and quantification of the analyte(s) of interest present in the sample when the analyte(s) reach the mass spectrometer. Typically, but not necessarily, the ISTD is an isotopically labeled variant (comprising e.g. at least one $^2H$, $^{13}C$, and/or $^{15}N$ etc. label) of the analyte of interest.

In addition to the pre-treatment, the sample may also be subjected to one or more enrichment steps, wherein the sample is subjected to one or more "enrichment methods" or "enrichment workflows". Well-known enrichment methods include but are not limited to chemical precipitation, the use of a solid phase, and chromatographic methods.

Chemical precipitation refers to the addition of chemical components to the sample, which cause certain constituents of the sample to participate. Exemplified, a well-known precipitation method is the addition of acetonitrile to the sample.

Solid phases include but are not limited to Solid Phase Extraction (SPE) cartridges, and beads. The term "bead" refers to non-magnetic, magnetic, or paramagnetic spherical particals. Beads may be coated differently to be specific for an analyte of interest. The coating may differ depending on the use intended, i.e. on the intended capture molecule. It is well-known to the skilled person which coating is suitable for which analyte. The beads may be made of various different materials. The beads may have various sizes and comprise a surface with or without pores.

The term "chromatography" refers to a process in which a chemical mixture carried by a liquid or gas is separated into components as a result of differential distribution of the chemical entities as they flow around or over a stationary liquid or solid phase.

The term "liquid chromatography" or "LC" refers to a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Methods in which the stationary phase is more polar than the mobile phase (e.g., toluene as the mobile phase, silica as the stationary phase) are termed normal phase liquid chromatography (NPLC) and methods in which the stationary phase is less polar than the mobile phase (e.g., water-methanol mixture as the mobile phase and C18 (octadecylsilyl) as the stationary phase) are termed reversed phase liquid chromatography (RPLC).

"High performance liquid chromatography" or "HPLC" refers to a method of liquid chromatography in which the degree of separation is increased by forcing the mobile phase under pressure through a stationary phase, typically a densely packed column. Typically, the column is packed with a stationary phase composed of irregularly or spherically shaped particles, a porous monolithic layer, or a porous membrane. HPLC is historically divided into two different sub-classes based on the polarities of the mobile and stationary phases, namely NP-HPLC and RP-HPLC.

Micro LC refers to a HPLC method using a column having a narrow inner column diameter, typically below 1 mm, e.g. about 0.5 mm. "Ultra high performance liquid chromatography" or "UHPLC" refers to a HPLC method using a high pressure of e.g. 120 MPa (17,405 lbf/in$^2$), or about 1200 atmospheres.

Rapid LC refers to an LC method using a column having an inner diameter as mentioned above, with a short length <2 cm, e.g. 1 cm, applying a flow rate as mentioned above and with a pressure as mentioned above (Micro LC, UHPLC). The short Rapid LC protocol includes a trapping/wash/elution step using a single analytical column and realizes LC in a very short time <1 min.

Further well-known LC modi include Hydrophilic interaction chromatography (HIC), size-exclusion LC, ion exchange LC, and affinity LC.

LC separation may be single-channel LC or multi-channel LC comprising a plurality of LC channels arranged in parallel. In LC analytes may be separated according to their polarity or log P value, size or affinity, as generally known to the skilled person.

In the context of the present disclosure, the term "first enrichment process", "first enrichment step", or "first enrichment workflow" refers to an enrichment process which occurs subsequent to the pre-treatment of the sample and provides a sample comprising an enriched analyte relative to the initial sample.

In the context of the present disclosure the term "second enrichment process", "second enrichment step", or "second enrichment workflow" refers to an enrichment process which occurs subsequent to the pre-treatment and the first enrichment process of the sample and provides a sample comprising an enriched analyte relative to the initial sample and the sample after the first enrichment process.

The term "chromatography" refers to a process in which a chemical mixture carried by a liquid or gas is separated into components as a result of differential distribution of the chemical entities as they flow around or over a stationary liquid or solid phase.

A "kit" is any manufacture article (e.g. a package or container) comprising at least one reagent, e.g., a medicament for treatment of a disorder, or a probe for specifically detecting an analyte of the present invention. The kit is preferably promoted, distributed, or sold as a unit for performing the method of the present invention. Typically, a kit may further comprise carrier means being compartmentalized to receive in close confinement one or more container means such as vials, tubes, and the like. In particular, a container means may comprise one of the separate elements to be used in the method of the first aspect. Kits may further comprise one or more other containers comprising further materials including but not limited to buffers, diluents, filters, needles, syringes, and package inserts with instructions for use. A label may be present on the container to indicate that the composition is used for a specific application, and may also indicate directions for either in vivo or in vitro use. The kit may also include a computer program code provided on a data storage medium or device such as an optical storage medium (e.g., a Compact Disc) or directly on a computer or data processing device. Moreover, the kit may comprise standard amounts for the biomarkers as described elsewhere herein for calibration purposes.

A "package insert" is used to refer to instructions customarily included in commercial packages of diagnostic products, that contain information about the indications, usage, performance, and/or warnings concerning the use of such diagnostic product.

Embodiments

A first aspect of the present invention refers to a method for determining glycated hemoglobin A (HbA1c) in a sample, comprising:

(a) providing a sample comprising hemoglobin A (HbA) molecules, (b) subjecting the sample from step (a) to a partial proteolytic digestion step wherein N-terminal fragments of hemoglobin A β-chain molecules are generated, (c) optionally enriching the N-terminal fragments of hemoglobin A β-chain molecules generated in step (b), and (d) subjecting the sample comprising N-terminal fragments of hemoglobin A β-chain molecules to an analysis by mass-spectrometry (MS) wherein the amount or concentration of HbA1c in the sample is determined.

Thereby, the amount or concentration of HbA1c, in particular the relative amount of HbA1c, i.e. the ratio of glycated HbA1c molecules to non-glycated HbA0 molecules or to HbA molecules in total, in a sample can be determined. The method is highly accurate and gives coefficient of variation (CV) of 2.5% or less, particularly of 2.0% or less, more particularly 1.5% or less, when repeatedly determining the amount of HbA1c, the ratio of HbA1c/HbA, or the ratio HbA1c/HbA0 in a given sample.

According to step (a) a sample comprising hemoglobin molecules is provided. The sample is preferably a hemolysed whole blood sample, particularly a hemolysed human whole blood sample, e.g. derived from a subject the blood of which to be tested for the amount of glycated hemoglobin A. Hemolysis is particularly carried out by dilution with water (H$_2$O), e.g. deionized or distilled water, in particular in a ratio of sample:water of about 1:2 to about 1:20, in particular about 1:5 to about 1:10, in particular about 1:9 (v/v). The sample may be hemolysed for a time less than about 30 min, less than about 10 min, less than about 5 min or even less than about 2 min. In particular embodiments, the sample is hemolyzed for a time of about 10 to about 60 sec.

In particular embodiments, the hemolysis is carried out by mixing sample and water, in particular by vortexing sample and water. In particular sample and water are mixed, in particular vortexed, for about 1 to about 60 sec, in particular for about 5 to about 30 sec, in particular for about 10 sec.

During hemolysis the sample may be kept at a temperature of 20° C. to 30° C., in particular at 22-25° C., in particular at room temperature.

In particular embodiments, the hemolysis of the sample is carried out by mixing the sample with water in a ratio of 1:9 by vortexing for 10 sec at room temperature.

Step (b) of the method of the invention comprises a partial proteolytic digestion of HbA molecules in the sample. Surprisingly, it was found that when subjecting hemoglobin A molecules present in a sample to a partial proteolytic digestion, the amount of digestion products is sufficient to allow an accurate determination of HbA1c in the sample. Thus, a rapid and reliable method for determination of HbA1c is provided. The partial proteolytic digestion results in a mixture comprising intact HbA molecules and proteolytically digested HbA molecules, in particular a mixture of intact HbA1c β-chain molecules, intact HbA0 β-chain molecules, proteolytically digested HbA1c β-chain molecules and proteolytically digested HbA0 β-chain molecules. In preferred embodiments, the partial proteolytic digestion in step (b) comprises a digestion wherein about 1% to about 20%, particularly about 5% to 10% of the HbA β-chain molecules present in the sample are digested based on the total amount of HbA β-chain molecules originally present in the sample.

The partial proteolytic digestion in step (b) of the method of the invention is carried out with a proteolytic enzyme under conditions wherein proteolytic cleavage of HbA β-chain molecules takes place. Preferably, a proteolytic enzyme is selected which—based on its cleavage specificity—generates an N-terminal fragment of the hemoglobin A β-chain molecule having a length in the range of 4 to 20 amino acids, particularly in the range of 5 to 15 amino acids. More preferably, the proteolytic enzyme cleaves the N-terminus of the human HbA β-chain molecule as shown in SEQ ID No: 1 after amino acid position 6, 8, or 14.

In particular embodiments, the partial proteolytic digestion in step (b) is carried out using an endopeptidase, particularly an endopeptidase selected from the group consisting of Glu-C, trypsin, pepsin, and thermolysin. Proteolytic digestion with Glu-C results in an N-terminal fragment of 6 amino acids, proteolytic digestion with trypsin results in an N-terminal fragment of 8 amino acids and proteolytic digestion with pepsin results in an N-terminal fragment of 14 amino acids. In a particular embodiment, the proteolytic digestion is carried out with the endopeptidase Glu-C.

In particular embodiments the present invention, the partial proteolytic digestion in step (b) is carried out for a period of about 10 min to about 120 min, e.g. for a time period of about 60 min or less, about 45 min or less or about 30 min or less. In particular embodiments, the partial proteolytic digestion is carried out for about 15 min to about 45 min.

In particular embodiments, the partial proteolytic digestion in step (b) is carried out at a temperature range from about 20° C. to about 40° C., in particular from about 25° C. to about 37° C., in particular from about 30° C. to about 37° C. In particular embodiments, the partial proteolytic digestion is carried out at 37° C.

In embodiments, the buffer used for the partial proteolytic digestion in step (b) is a buffer which does not comprise Na$^+$ and/or K$^+$ ions, in particular a buffer comprising ammonium ions such as an ammonium acetate or ammonium citrate buffer, e.g. comprising about 20 mM to about 50 mM ammonium acetate, or about 30 mM ammonium acetate.

In embodiments, the pH of the digestion buffer will depend on the specific proteolytic enzyme. In embodiments, wherein Glu-C is used as proteolytic enzyme the digestion buffer has an acidic pH, e.g. a pH of about 4 to about 5, in particular a pH of about 4.2 to about 4.5, or a pH of about 4.3.

In embodiments, the protease in step (b) is present in any suitable concentration in order to obtain the desired degree of partial digestion. In embodiments, the proteolytic enzyme, e.g. the endopeptidase Glu-C has a concentration of about 0.1 to about 1 mg/mL, in particular of 0.3 mg/ml to 0.8 mg/ml, particularly of about 0.6 mg/mL. In particular embodiments, wherein Glu-C is used as the proteolytic enzyme, the concentration used in the partial proteolytic digestion in step (b) is about 0.6 mg/mL.

In particular embodiments, the partial proteolytic digestion in step (b) is carried out using the endopeptidase Glu-C for about 45 min at a temperature of about 37° C.

In particular embodiments, the partial proteolytic digestion in step (b) is carried out using the endopeptidase Glu-C at a concentration of about 0.6 mg/ml for about 45 min at a temperature of about 37° C.

In particular embodiments, the partial proteolytic digestion in step (b) is carried out using the endopeptidase Glu-C at a concentration of about 0.6 mg/mi in 30 mM ammonium acetate buffer, for about 45 min at a temperature of about 37° C.

In particular embodiments, the partial proteolytic digestion in step (b) is carried out using the endopeptidase Glu-C at a concentration of 0.6 mg/ml in 30 mM ammonium acetate buffer at a pH of about 4.3, for about 45 min at a temperature of about 37° C.

In particular embodiments of the invention, the partial proteolytic digestion in step (b) is stopped after having achieved the desired degree of proteolytic cleavage. For example, the digestion may be stopped by adding a stopping medium which is capable of stopping or stops the proteolytic digestion. In particular embodiments the stopping agent is a dilution medium, e.g. an acidic solution, in particular an acidic solution comprising formic acid (FA). In embodiments, said acidic solution comprises FA in water. In embodiments wherein FA is used in the acidic solution to stop the partial proteolytic digestion in step (b) FA may be present at a concentration of 0.05% to 0.2% (v/v) FA, in particular in a concentration of about 0.1% (v/v) FA. In embodiments, the acid, in particular the FA, adjusts the pH to about 1 to about 4. In particular the pH is adjusted to about 2.7.

In particular embodiments, the partial proteolytic digestion in step (b) is carried out using the endopeptidase Glu-C at a concentration of about 0.6 mg/ml in about 30 mM ammonium acetate buffer at a pH of about 4.3, for about 45 min at a temperature of about 37° C., and is stopped after using a dilution buffer comprising about 0.1% (v/v) FA in water to adjust a pH of about 2.7.

In particular embodiments, the sample obtained after the partial proteolytic digestion of step (b) may be further subjected to an analyte enrichment workflow, i.e. the enrichment step (c) which comprises enriching proteolytically generated N-terminal fragments of the hemoglobin A β-chain in the sample. The term "enriching" proteolytically generated N-terminal fragments is understood as increasing the relative amount of N-terminal fragment molecules versus other sample constituents before subjecting the sample to analysis by MS. In particular, the enriching step comprises an enrichment of N-terminal hemoglobin A β-chain fragments whilst other sample constituents potentially interfering with the measurement are depleted or removed. In particular embodiments, the N-terminal hemoglobin A β-chain fragments are enriched by at least a factor of about 2, by at least a factor of about 5, or by at least a factor of about 10.

The enrichment step (c) may include one or more enrichment methods, in particular a first and/or a second enrichment step. Enrichment methods are well-known in the art and include but are not limited to chemical enrichment methods including but not limited to chemical precipitation, and enrichment methods using solid phases including but not limited to solid phase extraction methods, bead workflows, and chromatographic methods (e.g. gas or liquid chromatography). Accordingly, in particular embodiments, enrichment step (c) comprise one or more enrichment methods selected from the group consisting of chemical precipitation, methods using solid phase extraction methods, bead workflows, and chromatographic methods.

In embodiments, enrichment step (c) comprises one or two enrichment methods, i.e. comprises enrichment step (c)(i) and/or enrichment step (c)(ii). In embodiments, wherein the method comprises enrichment step (c)(i) and enrichment step (c)(ii), enrichment step (c)(i) is performed prior to enrichment step (c)(ii).

In embodiments, a first enrichment step (c)(i) comprises a bound/free separation step comprising the addition of a solid phase carrying analyte-selective groups to the pretreated sample. The solid phase may be comprised of solid particles or of a non-particular solid phase, e.g. a coated surface within a vessel or a well. In particular embodiments, the solid phase is comprised of magnetic or paramagnetic particles, in particular particles having a magnetic or paramagnetic core. In embodiments, said magnetic or paramagnetic core comprises a metal oxide and/or a metal carbide. In an especially particular embodiment, the core comprises $Fe_3O_4$.

The surface of the solid phase, in particular the magnetic or paramagnetic beads, may be a hydrophobic surface, in particular comprising hydrophobic organic groups such as $C_3$-$C_{18}$ alkyl groups, more particularly $C_4$ alkyl groups. Further, the hydrophobic surface of the solid phase, in particular the surface of the magnetic or superparamagnetic beads, comprises pores. The pore size may be in the range of from 1 nm to 200 nm, in particular less than about 100 nm, in particular less than about 10 nm. Suitable hydrophobic surfaces may e.g. be found in "The HPLC Expert: Possibilities and Limitations of Modern High Performance Liquid Chromatography" DOI:10.1002/9783527677610

In embodiments, enrichment step (c) comprises a first enrichment step (c)(i), using magnetic or paramagnetic beads. In embodiments, a first enrichment step (c) (i) comprises the addition of magnetic or paramagnetic beads carrying groups for the selective binding of proteolytically generated N-terminal fragments of hemoglobin A β-chain molecules present in the sample. In embodiments, the addition of the magnetic beads comprises agitation or mixing. A pre-defined incubation period for capturing the proteolytically generated N-terminal fragments of hemoglobin A β-chain molecules on the bead follows. In embodiments, the workflow comprises a washing step (W1) after incubation with the magnetic beads. Depending on the analyte(s) one or more additional washing steps (W2) are performed. One washing step (W1, W2) comprises a series of steps including magnetic bead separation by a magnetic bead handling unit comprising magnets or electromagnets, aspiration of liquid, addition of a washing buffer, resuspension of the magnetic beads, another magnetic bead separation step and another aspiration of the liquid. Moreover, washing steps may differ in terms of type of solvent (water/organic/salt/pH), apart from volume and number or combination of washing cycles. It is well-known to the skilled person how to choose the respective parameters. The last of the washing steps (W1, W2) is followed by the addition of an elution reagent followed by resuspension of the magnetic beads and a pre-defined incubation period for releasing the analyte(s) of interest from the magnetic beads. The bound-free magnetic beads are then separated and the supernatant containing N-terminal hemoglobin A β-chain fragments is captured.

In embodiments, contacting of the sample comprising N-terminal hemoglobin A β-chain fragments with the solid phase preferably takes place at an acidic pH, e.g. at a pH of about 1 to about 4, particularly at a pH of about 2.7. For this purpose, a sample, e.g. a hemolysed whole blood sample, may be diluted after partial proteolytic digestion with an acidic medium, e.g. formic acid as described above in a concentration of about 0.01% to about 0.2% (v/v), e.g. about 0.1% (v/v), to obtain the desired pH.

Selective elution of bound proteolytically generated N-terminal fragments of hemoglobin A β-chain molecules from the solid phase may be performed by contacting the loaded solid phase with an elution medium, which may be an aqueous solution comprising an organic water-miscible solvent, in particular acetonitrile, or methanol, in an amount of about 5 to about 20% (v/v), e.g. about 10% (v/v). The elution medium is preferably an acidic medium, in particular comprising formic acid. The aqueous portion of the elution medium may be substantially the same as described for the solid phase binding medium, e.g. an acidic medium having a pH of about 1 to about 4, e.g. a pH of about 2.7.

Alternatively or additionally, enrichment step (c) may comprise a second enrichment step (c)(ii). In the second enrichment step (c)(ii), N-terminal hemoglobin A β-chain fragments are further enriched in the sample. In particular embodiments, enrichment step (c)(ii) comprises a chromatographic step, wherein individual constituents of the sample are separated from each other. In embodiments, the second enrichment step (c)(ii) may be performed subsequently to the partial proteolytical digestion of step (b) as described in detail above, or may be performed subsequent to the first enrichment step (c)(i) as described in detail above.

In the second enrichment step (c)(ii), chromatographic separation is used to further enrich the analyte of interest in the sample. In embodiments, the chromatographic separation is gas or liquid chromatography. Both methods are well known to the skilled person. In embodiments, the liquid chromatography is selected from the group consisting of HPLC, rapid LC, micro-LC, flow injection, and trap and elute. In particular embodiments, the chromatographic separation comprises the use of a single chromatic column, or the use of two or more chromatic columns. In particular embodiments, wherein two or more chromatic columns are used, the columns are positioned downstream of each other, i.e. a second column is positioned downstream of a first column, and an optional third column is position downstream of the second column, etc.. In embodiments wherein two or more columns are used, these columns may be identical or may differ from each other depending on the desired function. It is well-known to the skilled person to choose the correct columns and set up.

In embodiments, the sample obtained after the proteolytic digestion step (b) or the first enrichment step (c)(i) is transferred to an LC station or is transferred to the LC station after a dilution step by addition of a dilution liquid. Different elution procedures/reagents may also be used, by changing e.g. the type of solvents (water/organic/salt/pH) and volume. The various parameters are well-known to the skilled person and easily chosen.

In particular embodiments, enrichment step (c) comprises a first enrichment step (c)(i) and a second enrichment step (c)(ii), in particular wherein the second enrichment step (c)(ii) is performed subsequent to the first enrichment step (c)(i). In particular embodiments, the first enrichment step (c)(i) comprises bead workflow as described in detail above, and the second enrichment step (c)(ii) comprises liquid chromatography, in particular selected from the group consisting of HPLC, rapid LC, micro-LC, flow injection, and/or trap and elute.

According to the present invention, step (d) of the method of the present invention comprises an analysis of N-terminal fragments of hemoglobin A β-chain molecules, which have been generated by partial digestion with a protease such as pepsin, trypsin or Glu-C, and which have been separated from non-digested intact hemoglobin A β-chain molecules before MS analysis.

The analysis according to step (d) of is carried out by MS. Preferably the MS analysis procedure comprises a tandem MS (MS/MS) analysis, particularly a triple quadrupole (Q) MS/MS analysis.

In embodiments, the mass spectrometric analysis step (d) comprises:

(i) subjecting an ion of the proteolytically generated N-terminal fragments of hemoglobin A β-chain molecules to a first stage of mass spectrometric analysis, whereby the parent ion of the proteolytically generated N-terminal fragments of hemoglobin A β-chain molecules is characterised according to its mass/charge (m/z) ratio, (ii) causing fragmentation of the parent ion, wherein the daughter ion of the proteolytically generated N-terminal fragments of hemoglobin A β-chain molecules differs in its m/z ratio from the parent ion of the proteolytically generated N-terminal fragments of hemoglobin A β-chain molecules, and (iii) subjecting the daughter ion to a second stage of mass spectrometric analysis, whereby the daughter ion is characterized according to its m/z ratio. The method of the invention comprises a quantitative determination of HbA1c in the sample. In particular, the relative amount of glycated HbA1c molecules to non-glycated HbA0 molecules or to HbA molecules in total is determined. In an especially preferred embodiment, this relative amount is determined with a coefficient of variation (CV) of 2.5% or less, particularly of 2.0% or less, more particularly of 1.5% or less.

In an especially preferred embodiment, the method of the invention comprises a workflow as follows:

(a) hemolysing a whole blood sample, e.g. by dilution with $H_2O$, (b) subjecting the sample from step (a) to a partial proteolytic digestion with the endoproteinase Glu-C, wherein N-terminal fragments of hemoglobin A β-chain molecules are generated and stopping the digestion by adding diluted acid, e.g. formic acid, (c) enriching the N-terminal fragments of hemoglobin A β-chain molecules generated in step (b) by contacting the sample with a solid phase, particularly comprised of magnetic or paramagnetic particles, in particular having a hydrophobically modified surface, under conditions wherein proteolytically generated N-terminal fragments of hemoglobin A β-chain molecules bind to the solid phase, and selectively eluting the bound fragments from the loaded solid phase, and (d) subjecting the sample from step (c) comprising N-terminal fragments of hemoglobin A β-chain molecules to an analysis by MS, in particular tandem mass-spectrometry (MS/MS), in particular triple quadruple tandem MS, wherein the amount or concentration of HbA1c in the sample is determined.

In further embodiments of the first aspect, the method of determining glycated hemoglobin A (HbA1c) in a sample comprises the additional step of adding an internal standard (ISTD) to the sample. In embodiments, the internal standard is added to the sample before or after the partial proteolytic digestion step (b). In case the internal standard is added before the partial proteolytic digestion step (b), the internal standard is preferably an isotopically labeled intact hemoglobin molecule. In case the internal standard is added after the partial proteolytic digestion step (b), the internal standard is preferably an isotopically labeled HbA1c peptide. In embodiments the isotopically labeled ISTD comprises at least one $^2H$, $^{13}C$, and/or $^{15}N$ label.

A second aspect of the present invention refers to a kit, particularly suitable for performing the method as described above, comprising (i) an enzyme for the partial proteolytic digestion of HbA β-chain molecules and optionally a digestion buffer for said enzyme, (ii) a stopping medium, which is capable of stopping or stops a proteolytic digestion with the enzyme of (i), and (iii) optionally enrichment means for enriching the proteolytically digested HbA1c molecules, and (iv) optionally an elution medium comprising an organic water-miscible solvent for use in eluting sample components from the enrichment means of (iii).

With regard to particular embodiments of the second aspect of the present invention, reference is made to all embodiments described above in detail in context with the first aspect.

In embodiments of the second aspect of the present invention, the enzyme comprised in the kit is selected from the group consisting of Glu-C, trypsin and pepsin. In particular embodiments, the comprised enzyme is Glu-C.

In embodiments of the second aspect, the enzyme, in particular Glu-C, is comprised in a buffer which does not comprise $Na^+$ and/or $K^+$ ions, in particular in a buffer comprising ammonium ions such as an ammonium acetate or ammonium citrate buffer. In particular embodiments, Glu-C is comprised in a buffer comprising about 20 mM to about 50 mM ammonium acetate, or about 30 mM ammonium acetate.

In embodiments, the pH of the digestion buffer will depend on the specific proteolytic enzyme. In embodiments, wherein Glu-C is comprised in the kit, the digestion buffer has an acidic pH, in particular a pH of about 4 to about 5, in particular a pH of about 4.2 to about 4.5, particularly a pH of about 4.3.

In embodiments, the enzyme, in particular the Glu-C, is present in any suitable concentration in order to obtain the desired degree of partial proteolytic digestion. In embodiments, the proteolytic enzyme, in particular the Glu-C, comprised in the kit has a concentration of about 1 to about 5 mg/mL, in particular of 2 mg/ml to 3 mg/ml, particularly of about 2 mg/mL. In particular embodiments, wherein Glu-C is used as the proteolytic enzyme, the concentration comprised in the kit is about 2 mg/mL.

In embodiments, the kit further comprises a stopping medium, e.g. a dilution medium, which is capable of stopping or stops the proteolytic digestion. In embodiments, the dilution medium is an acidic solution comprising formic acid (FA). In embodiments, said acidic solution comprises FA in water. In embodiments, the dilution medium comprises a concentration of 0.05% to 0.2% (v/v), in particular in a concentration of about 0.1% (v/v) FA in water. In embodiments, the acid is present in an amount to adjust the pH of a sample to be analyzed to a pH of about 1 to about 4, in particular the pH is adjusted to about 2.7.

In embodiments, the kit comprises enrichment means adapted for carrying out at least one enrichment step, in particular a bound/free separation step and/or a chromatographic step. In embodiments, the enrichment means comprises a solid phase which may be comprised of solid particles, e.g. magnetic or paramagnetic particles, or of a non-particular solid phase.

In particular embodiments the solid phase carries groups for the selective binding of proteolytically generated N-terminal fragments of hemoglobin A β-chain molecules, e.g. hydrophobic organic groups. In further particular embodiments, the enrichment means may comprise a chromatographic column, in particular a chromatographic column for performing a chromatographic step.

In embodiments, the elution medium optionally comprised in the kit comprises an aqueous solution comprising an organic water-miscible solvent, in particular acetonitrile (ACN). The organic water-miscible solvent, in particular the ACN is present in an amount of about 5 to about 20%, e.g. of about 10% (v/v).

The kit may be provided as a single package comprising containers of the individual components or as a set of several packages each comprising a container of the individual components.

In embodiments, the kit further comprises a package insert. In embodiments, the package insert comprises information on the indications, usage, performance, and/or warnings concerning the kit.

A third aspect of the present invention is a diagnostic system adapted for determining glycated HbA1c in a sample; in particular by performing the method as described above.

In particular embodiments, the diagnostic system comprises:

(i) at least one station for the preparation of samples comprising N-terminal fragments of HbA1c molecules, wherein the preparation comprises a partial proteolytic digestion of hemoglobin A (HbA) molecules.

(ii) optionally at least one enrichment station adapted for selectively enriching N-terminal fragments of hemoglobin A β-molecules from the sample, and (iii) at least one station adapted for the analysis of N-terminal fragments of hemoglobin A molecules by mass-spectrometry (MS) and determining the amount or concentration of HbAc1 in the sample.

With regard to particular embodiments of the third aspect of the present invention, reference is made to all embodiments described above in detail in context with the first and second aspect.

In particular embodiments, the diagnostic system is adapted for allowing a high-throughput of samples, in particular for allowing a throughput of up to 100 samples/hour or more. For example, a system as described in WO 2017/103180, incorporated herein by reference, may be used.

In particular embodiments, the diagnostic system comprises at least one station for random access sample preparation, and at least one station for the enrichment of the N-terminal fragments of hemoglobin A β-chain molecules before MS analysis.

In embodiments, such a diagnostic system comprises a sample preparation station for the automated preparation of samples comprising N-terminal fragments of hemoglobin A β-chain molecules. In particular embodiments, said station comprises a section for hemolysing one or more samples and a section for providing a partial proteolytical digestion of HbA molecules in one or more samples.

In embodiments, said diagnostic system further comprises an enrichment station. Said enrichment station comprises a section for contacting one or more samples after partial proteolytic digestion with enrichment means, in particular with a solid phase, in particular magnetic or paramagnetic particles. Additionally or alternatively, the enrichment station comprises a chromatographic section, in particular an LC section. In embodiments, the LC section comprises one or more LC channels. In embodiments, wherein the LC section comprises more than one LC channel, the channels may be arranged in parallel.

In embodiments, the diagnostic system comprises at least one interface between the different sections and stations for inputting the previously prepared samples into the subsequent section or station.

In embodiments, the diagnostic system further comprises a controller which may be programmed to assign samples to pre-defined sample preparation and enrichment workflows each comprising a pre-defined sequence of sample preparation and enrichments steps and requiring a pre-defined time for completion.

In particular embodiments, the controller plans an enrichment station channel input sequence for inputting the prepared samples that allows N-terminal fragments of HbA β-chain molecules from different enrichment station channels to elute in a non-overlapping eluate output sequence based on expected elution times.

In embodiments, the controller sets and initiates a sample preparation start sequence that generates a prepared sample output sequence out of the sample preparation station that matches the enrichment station channel input sequence so that when preparation of a sample is completed the assigned enrichment station channel is also available and the prepared sample can be inputted into the assigned enrichment station channel, before preparation of another sample is completed or before the next prepared sample arrives to the sample preparation/enrichment interface.

In embodiments, the controller sets a reference period for the appropriate timing of workflows. This makes it possible to coordinate the following processing steps: (1) start preparation of at most one sample per reference period with possible one or more reference periods between consecutive samples in the sample preparation start sequence; and/or (2) complete preparation of at most one sample per reference period with possible one or more reference periods between consecutive prepared samples of the prepared sample output sequence; and/or (3) input one prepared sample per reference period into one of the enrichment station channels with possible one or more reference periods between consecutive enrichment station channel inputs; and/or (4) output one enrichment station eluate per reference period with possible one or more reference periods between consecutive enrichment station eluates.

In particular, the present invention relates to the following items:

1. A method for determining glycated hemoglobin A (HbA1c) in a sample, comprising:
    (a) providing a sample comprising hemoglobin A (HbA) molecules,
    (b) subjecting the sample from step (a) to a partial proteolytic digestion step, wherein N-terminal fragments of hemoglobin A β-chain molecules are generated,
    (c) optionally enriching the N-terminal fragments of hemoglobin A β-chain molecules generated in step (b), and
    (d) subjecting the sample comprising N-terminal fragments of hemoglobin A β-chain molecules to an analysis by mass-spectrometry (MS) wherein the amount or concentration of HbA1c in the sample is determined.

2. The method of item 1, wherein the sample in step (a) is a hemolysed whole-blood sample, particularly a hemolysed human whole-blood sample.

3. The method of item 1 or 2, wherein the sample in step (a) is hemolysed using water ($H_2O$), e.g. in a ratio of sample:water of about 1.2 to about 1:20 such as in a ratio of about 1:5, about 1:10, or about 1:9 (v/v).

4. The method of any one of items 1-3, wherein the sample is hemolysed for a time period of less than of 30 min, less than about 10 min, or less than about 5 min, in particular for a time of about 10 to about 60 sec.

5. The method of any of items 1-4, wherein in the partial proteolytic digestion step (b) about 1% to about 20%, particularly about 5% to 10% of the HbA β-chain molecules present in the sample are digested based on the total amount of HbA β-chain molecules originally present in the sample.

6. The method of any one of items 1-5, wherein the partial proteolytic digestion in step (b) is carried out with a proteolytic enzyme which generates an N-terminal fragment of the hemoglobin A β-chain molecule having a length in the range of 4-20 amino acids, particularly in the range of 5-15 amino acids, and more particularly wherein the proteolytic enzyme cleaves a hemoglobin A β-chain molecule after amino acid position 6, 8, or 14 according to SEQ ID NO: 1.

7. The method of any one of items 1-6, wherein the partial proteolytic digestion in step (b) is carried out with an endopeptidase, particularly with an endopeptidase selected from the group consisting of Glu-C, trypsin, pepsin, and thermolysin.

8. The method of any one of items 1-7, wherein the partial proteolytic digestion in step (b) is carried out for a time period of less than about 60 min, in particular less than about 45 min, or less than 30 min.

9. The method of any one of items 1-8, wherein the partial proteolytic digestion in step (b) is carried out at a temperature range from about 20° C. to about 40° C. or from about 25° C. to about 37° C.

10. The method of any one of items 1-9, wherein the digestion buffer in step (b) is a buffer comprising ammonium ions such as an ammonium acetate or ammonium citrate buffer, e.g. comprising about 20 to about 50 mM ammonium acetate, particularly about 30 mM ammonium acetate.

11. The method of any one of items 1-10, wherein the digestion buffer has a pH of about 4 to about 5, particularly a pH of about 4.3.

12. The method of any one of items 1-11, wherein the proteolytic enzyme in step (b) is present in a concentration of about 0.1 to about 1 mg/mL, particularly of about 0.6 mg/mL.

13. The method of any one of items 1-12, wherein the partial proteolytic digestion in step (b) is stopped, in particular by adding an acidic medium such as formic acid (FA), particularly about 0.1% (v/v) FA in water.

14. The method of any one of items 1-13, wherein the proteolytic digestion in step (b) is carried out with the endopeptidase Glu-C, particularly in a concentration of about 0.6 mg/mL for a time period of about 15 min to about 45 min at a temperature of about 37° C., in a buffer comprising ammonium ions, and the digestion is stopped by adding formic acid in water, particularly 0.1% (v/v) FA in water.

15. The method of any one of items 1-14, wherein enrichment step (c) comprises a bound/free separation step (c) (i) comprising contacting the sample with a solid phase having a surface for the selective binding of proteolytically generated N-terminal fragments of the hemoglobin A β-chain under conditions wherein the proteolytically generated N-terminal fragments of the hemoglobin A β-chain bind to the solid phase, and selectively eluting the bound fragments from the solid phase.

16. The method of item 15, wherein the solid phase comprises a hydrophobic surface.

17. The method of item 15 or 16, wherein in step (c) (i) the sample is contacted with the solid phase at an acidic pH, particularly at a pH of about 1 to about 3, e.g. at a pH of about 2.

18. The method of any one of items 15-17, wherein the solid phase is comprised of particles, e.g. of magnetic or paramagnetic particles, e.g. particles having a magnetic or paramagnetic core comprising a metal oxide and/or a metal carbide, in particular $Fe_3O_4$.

19. The method of any one of items 15-18, wherein the hydrophobic surface of the solid phase comprises $C_3$-$C_{18}$ alkyl groups, particularly $C_4$ alkyl groups.

20. The method of any one of items 15-19, wherein the hydrophobic surface of the solid phase comprises pores having a pore size of less than about 100 nm, in particular less than about 10 nm.

21. The method of any one of items 15-20, wherein N-terminal fragments of hemoglobin A β-chain molecules are enriched by selective elution from the solid phase, particularly in the presence of about 5-20% (v/v) acetonitrile, more particularly in the presence of about 10% (v/v) acetonitrile.

22. The method of any one of items 1-21, wherein step (c) comprises a chromatographic step (ii), in particular liquid chromatography such as HPLC, micro LC, or rapid LC, of the sample.

23. The method of any one of items 15-22 wherein enrichment step comprises a bound/free separation step (c) (i) and a chromatographic step (c) (ii).

24. The method of any one of items 1-23, wherein step (d) comprises an MS/MS analysis, particularly an MS/MS analysis of N-terminal fragments of hemoglobin A β-chain molecules.

25. The method of any one of items 1-24, wherein step (d) comprises a triple quadrupole-MS/MS analysis.

26. The method of any one of items 1-25, wherein the ratio of glycated hemoglobin A (HbA1c) to non-glycated hemoglobin A (HbA0) or to total hemoglobin A (HbA) is determined.

27. The method of item 26, wherein the ratio is determined with a coefficient of variation of 2.5% or less, particularly of 2.0% or less, more particularly 1.5% or less.

28. A kit comprising
   (i) an enzyme for the partial proteolytic digestion of HbA β-chain molecules and optionally a digestion buffer for said enzyme,
   (ii) a stopping medium, which is capable of stopping a proteolytic digestion with the enzyme of (i), and
   (iii) optionally enrichment means for enriching the proteolytically digested HbA1c molecules, and
   (iv) optionally an elution medium comprising an organic water-miscible solvent for use in eluting sample components from the enrichment means of (iii).

29. Use of the kit of item 28 in a method of any one of items 1-27.

30. A diagnostic system for determining glycated hemoglobin A (HbAc1) in a sample adapted for performing the method of any one of items 1-27.

31. A diagnostic system for determining glycated hemo-
globin A (HbAc1) in a sample comprising
  (i) at least one station for the preparation of samples
comprising N-terminal fragments of HbA1c mol-
ecules, wherein the preparation comprises a partial
proteolytic digestion of hemoglobin A (Hb1) mol-
ecules,
  (ii) optionally at least one enrichment station adapted
for selectively enriching N-terminal fragments of
hemoglobin A β-molecules from the sample, and
  (iii) at least one station adapted for the analysis of
N-terminal fragments of hemoglobin A molecules by
mass-spectrometry (MS) and determining the
amount or concentration of HbAc1 in the sample.

32. Use of the diagnostic system of item 30 or 31 in the
method of any one of items 1-27.

In the following, the present invention is explained in
more detail by the Examples.

EXAMPLES

Example 1

Determination of HbA1 Peptide Fragments in Whole Blood

A whole blood sample of 100 µL was diluted with 900 µL
$H_2O$ and mixed by vortex for 10 s until a clear solution was
obtained. Then, 5 µL of the hemolysed whole blood sample
was further diluted with 20 µL H2O. 5 µL of the diluted
hemolysed blood sample, 15 µL endoproteinase Glu-C (2
mg/mL) and 30 µL digestion buffer (50 mM ammonium
acetate pH 4.3) were added to a LoBind vial (Eppendorf)
and incubated for 45 min at 37° C. in order to provide a
partial digestion, e.g. a digestion of 1 to 20% of HbA
molecules present in the sample. The enzymatic reaction
was stopped by adding 950 µL of 0.1% (v/v) formic acid.

Then, several batches of 100 µL hydrophobic magnetic
beads (50 mg/mL) were provided. 200 µL of the digested
whole blood sample and 700 µL $H_2O$ with 0.1% (v/v) formic
acid were added to each batch of magnetic beads. The
mixtures were shaken at 37° C. and 1200 rpm for 5 min.

Next, the beads were washed two times using 900 µL
0.1% (v/v) aqueous formic acid. Subsequently, 900 µL
elution medium (water with 0.1% formic acid containing
different amounts of acetonitrile (ACN), i.e. 5% (v/v), 10%
(v/v), 15% (v/v), 20% (v/v) and 30% (v/v)) were added to
each batch of loaded beads. The mixtures were shaken at 37°
C. and 1200 rpm for 1 min and the supernatants were
collected.

From each batch, 500 µL elution medium were collected
for testing. 1 µL was injected on a reverse phase column (Symmetry C18 Sentry Guard Cartridge 300A, 3.5 µm,
2.1×10 mm; Waters). Then, an isocratic elution using 10%
aqueous ACN with 0.1% formic acid at 900 µL/min was
carried out. The total rum time was 12 s.

The parameters for MS/MS were as follows:
Ion Source Type: ESI
Spray Voltage:
  Static
  Positive Ion (V): 3500.00
  Negative Ion (V): 2500.00
  Sheath Gas (Arb): 50
  Aux Gas (Arb): 25
  Sweep Gas (Arb): 3
  Ion Transfer Tube Temperature (° C.): 350
  Vaporizer Temperature (° C.): 400

In Table 1 the measurement parameters for HbA0 and
HbA1c are indicated:

| | Com-<br>pound | Start<br>Time<br>(min) | End<br>Time<br>(min) | Polarity | Pre-<br>cursor<br>(m/z) | Product<br>(m/z) | Collision<br>Energy<br>(V) | RF<br>Lens<br>(V) |
|---|---|---|---|---|---|---|---|---|
| 1 | HbA0 | 0 | 0.6 | Positive | 348.288 | 236.968 | 22.944 | 47 |
| 2 | HbA1c | 0 | 0.6 | Positive | 429.342 | 245.054 | 16.522 | 52 |

Figure 1B:
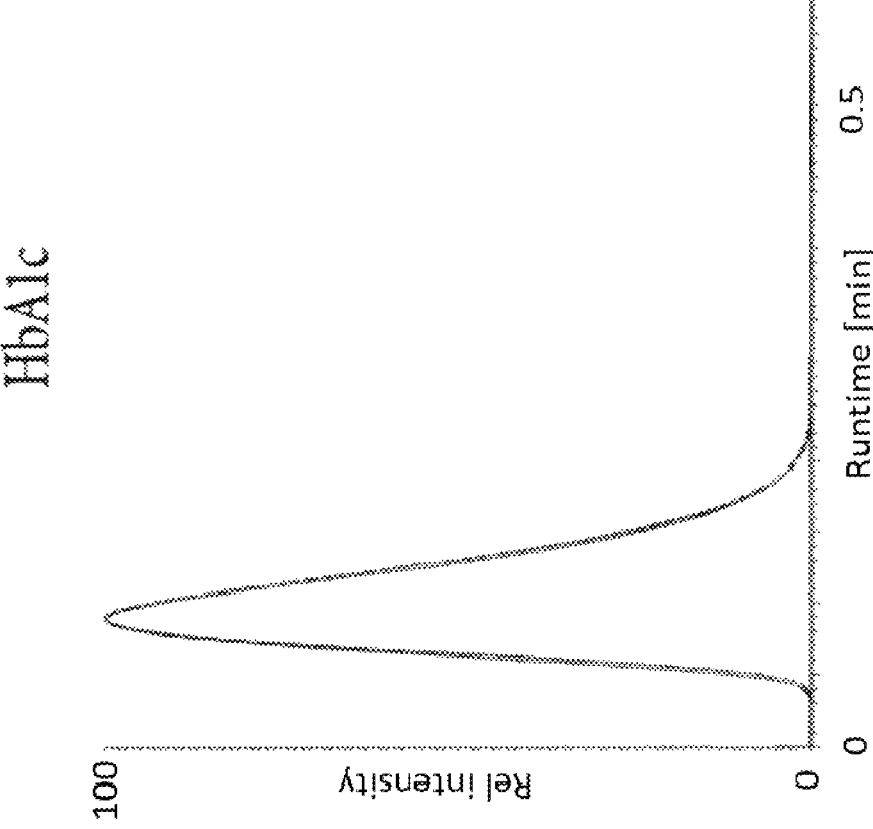

FIGS. 1A & 1B show the MS/MS peaks from HbA1c and
HbA0 peptides obtained by digestion of a whole blood
sample with Glu-C.

In Table 2 the measurement results for the coefficient of
variation (CV) of replicates (n=3) with regard to the
amounts of HbA0 and HbA1c and the ratio HbA1c/HbA0
obtained with different amounts of acetonitrile (ACN) in the
elution medium are indicated:

| | % RSD | HbA0 | HbA1c | HbA1c/HbA0 |
|---|---|---|---|---|
| Full Blood Bead Workflow 5%<br>ACN | | 0.5 | 2.7 | 3.1 |
| Full Blood Bead Workflow<br>10% ACN | | 1.2 | 2.0 | 1.0 |
| Full Blood Bead Workflow<br>15% ACN | | 0.7 | 1.1 | 0.6 |

Figure 2:
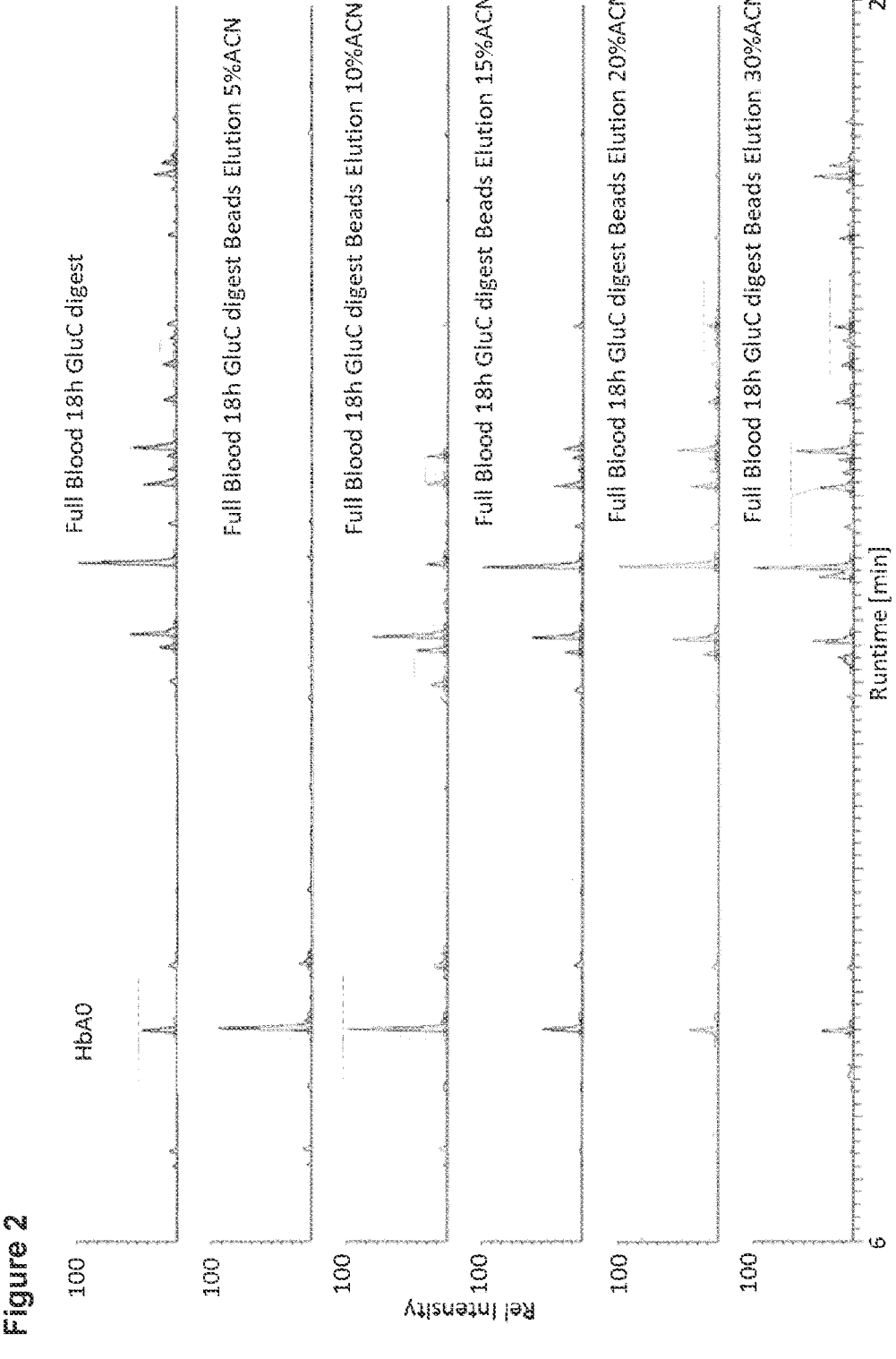
FIG. 2 depicts the results from digestion of whole blood samples with Glu-C without further purification (top) and with sample purification by enrichment on magnetic beads, followed by washing and elution with different concentrations ACN, namely 5% (v/v) ACN, 10% (v/v) ACN, 15% (v/v) ACN, 20% (v/v) ACN and 30% (v/v) ACN, respectively.

FIG. 2 shows the result from digestion of whole blood
samples with Glu-C without further purification (top) and
with sample purification by enrichment on magnetic beads,
followed by washing and elution with different concentra-
tions ACN, namely 5% (v/v) ACN, 10% (v/v) ACN, 15%
(v/v) ACN, 20% (v/v) ACN and 30% (v/v) ACN, respec-
tively. Elution with ACN, particularly in amounts of 5% or
10% ACN allows specific elution of HbA1c and HbA0 and
thus enrichment prior to LC-MS.

---

The invention claimed is:

1. A method for determining glycated hemoglobin A (HbA1c) in a sample, comprising:
   (a) providing a sample comprising hemoglobin A (HbA) molecules,
   (b) subjecting the sample from step (a) to a partial proteolytic digestion step wherein N-terminal fragments of hemoglobin A β-chain molecules are generated, wherein the partial proteolytic digestion is carried out with the endopeptidase Glu-C in a concentration of about 0.6 mg/mL for a time period of less than about 60 min at a temperature of about 37° C., in a buffer comprising ammonium ions, and stopping the partial proteolytic digestion by adding formic acid in water,
   (c) enriching the N-terminal fragments of hemoglobin A β-chain molecules generated in step (b), and
   (d) subjecting the sample comprising N-terminal fragments of hemoglobin A β-chain molecules to an analysis by mass-spectrometry (MS) wherein the amount or concentration of HbA1c in the sample is determined,
   wherein in the partial proteolytic digestion step (b) about 1% to about 20% of the HbA β-chain molecules present in the sample are digested based on the total amount of HbA β-chain molecules originally present in the sample.

2. The method of claim 1, wherein the sample in step (a) is a hemolysed whole-blood sample.

3. The method of claim 1, wherein the partial proteolytic digestion in step (b) is carried out with the endopeptidase Glu-C which generates an N-terminal fragment of the hemoglobin A ß-chain molecule having a length in the range of 4-20 amino acids.

4. The method of claim 1, wherein the partial proteolytic digestion in step (b) is carried out for a time period of about 15 min to about 45 min.

5. The method of claim 1, wherein in enriching step (c), N-terminal fragments of hemoglobin A β-chain molecules are enriched by selective elution from the solid phase.

6. The method of claim 1, wherein step (d) comprises an MS/MS analysis.

7. The method of claim 1, wherein the ratio of glycated hemoglobin A (HbA1c) to non-glycated hemoglobin A (HbA0) is determined.

8. The method of claim 1, wherein the partial proteolytic digestion in step (b) is carried out with the endopeptidase Glu-C, wherein the endopeptidase Glu-C cleaves a hemoglobin A ß-chain molecule after amino acid position 6, 8, or 14 according to SEQ ID NO: 1.

9. The method of claim 5, wherein in enriching step (c), N-terminal fragments of hemoglobin A β-chain molecules are enriched by selective elution from the solid phase-in the presence of about 5-20% (v/v) acetonitrile.

10. The method of claim 1, wherein the ratio of glycated hemoglobin A (HbA1c) to total hemoglobin A (HbA) is determined.

* * * * *